United States Patent
Radomyshelsky et al.

(10) Patent No.: US 8,673,126 B2
(45) Date of Patent: Mar. 18, 2014

(54) DYNAMIC PRECIOUS METAL ASSAY DEVICE

(75) Inventors: Leonid Radomyshelsky, San Diego, CA (US); Boris Loginov, San Diego, CA (US)

(73) Assignee: Tri Electronics, Inc, San Diego, CA (US)

( * ) Notice: Subject to any disclaimer, the term of this patent is extended or adjusted under 35 U.S.C. 154(b) by 254 days.

(21) Appl. No.: 13/405,370

(22) Filed: Feb. 27, 2012

(65) Prior Publication Data

US 2013/0220807 A1    Aug. 29, 2013

(51) Int. Cl.
*G01N 27/28* (2006.01)

(52) U.S. Cl.
USPC ......... 204/400; 205/790; 422/82.02; 324/693

(58) Field of Classification Search
USPC .................. 204/400, 416–419; 205/790, 795; 422/82.02, 408, 430; 401/198, 203, 401/204, 205, 206; 436/80; 324/446, 450, 324/437, 691, 693, 696, 724
See application file for complete search history.

(56) References Cited

U.S. PATENT DOCUMENTS

| 4,799,999 A | 1/1989 | Medvinsky |
| 5,128,016 A | 7/1992 | Moment |
| 5,218,303 A | 6/1993 | Medvinsky |
| 6,051,126 A | 4/2000 | Fegan, Jr. |
| 8,211,366 B2 * | 7/2012 | Ebersole et al. ........... 422/82.02 |
| 2008/0078677 A1 * | 4/2008 | Chua et al. ................... 204/406 |

* cited by examiner

*Primary Examiner* — Luan Van
*Assistant Examiner* — Gurpreet Kaur
(74) *Attorney, Agent, or Firm* — Selwyn S. Berg

(57) ABSTRACT

A DYNAMIC PRECIOUS METAL ASSAY DEVICE is described which is based on the methodology of the parent patent DYNAMIC PRECIOUS METAL ASSAY METHOD, U.S. Pat. No. 4,799,999 and achieves a highly accurate gold assay with a range extended to over 24 karats. The specified device requires a manual expulsion of a small amount of electrolyte from a disposable cartridge into a miniature galvanic cell which is formed at the lower tip of the device pencil. Placing the said tip against a gold specimen under test, thereby wetting it, and then by initiating the charging cycle and interpolating algorithm in the external electronics results in a professionally accurate assay of the gold specimen under test. The superior performance of this device is attributed to the novel replaceable electrolytic cartridge and miniature galvanic cell which wets a specimen through a porous interface. This improved device is very stable, rugged and is easily maintained.

3 Claims, 4 Drawing Sheets

The Pencil Assembly and External Electronics Box

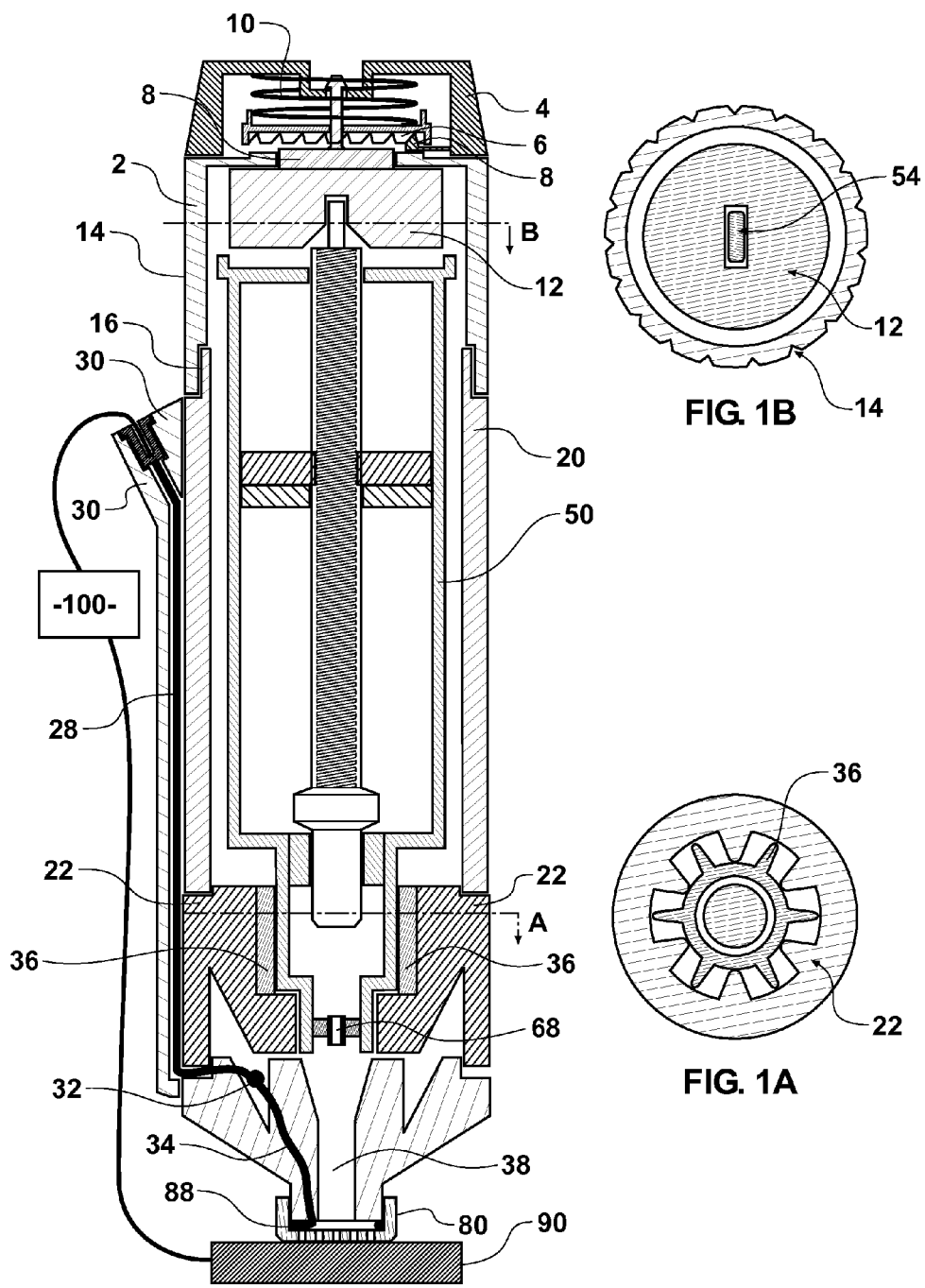
Figure 1- The Pencil Assembly and External Electronics Box

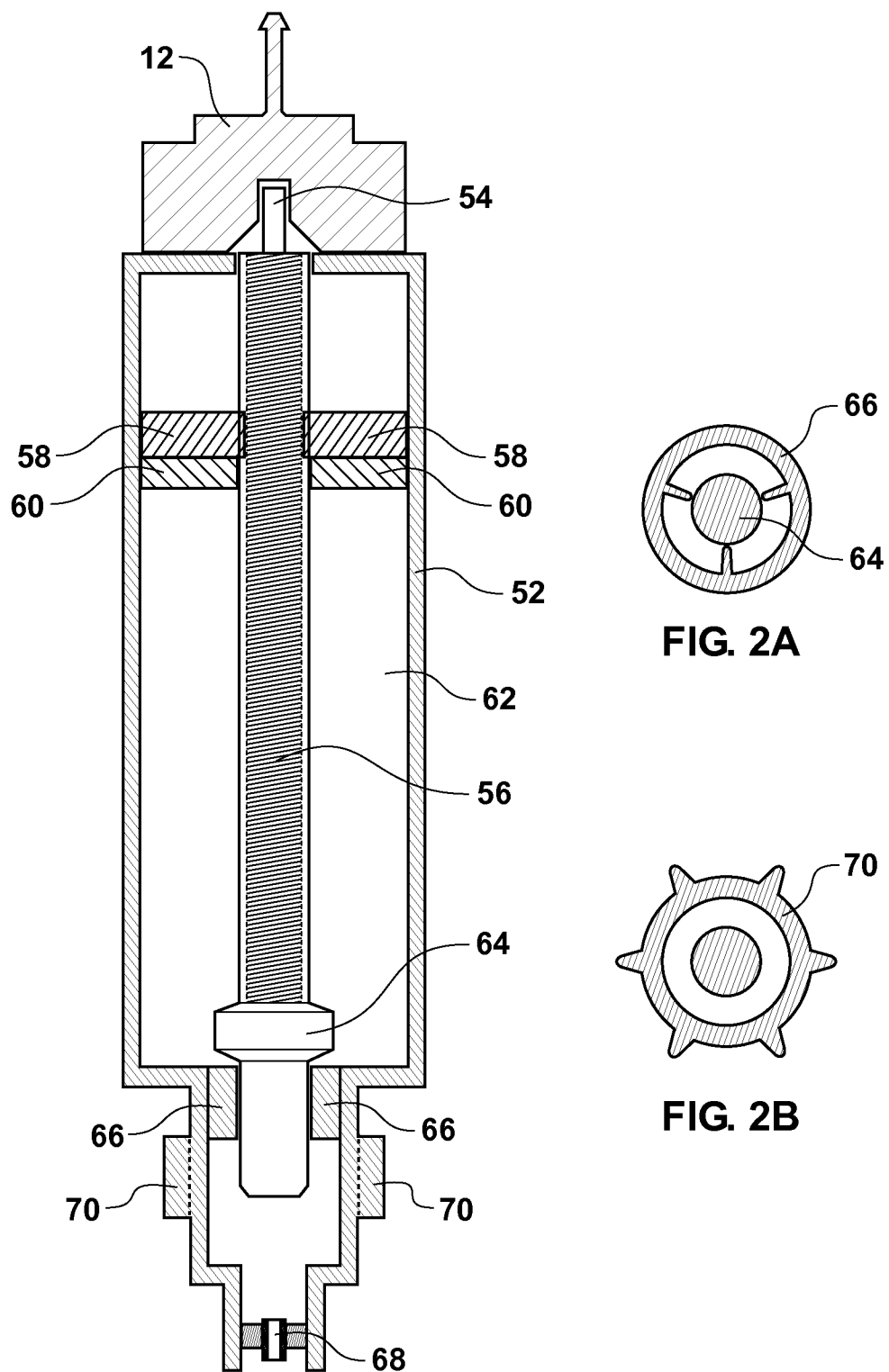
Figure 2- The Expendable Piston Cartridge

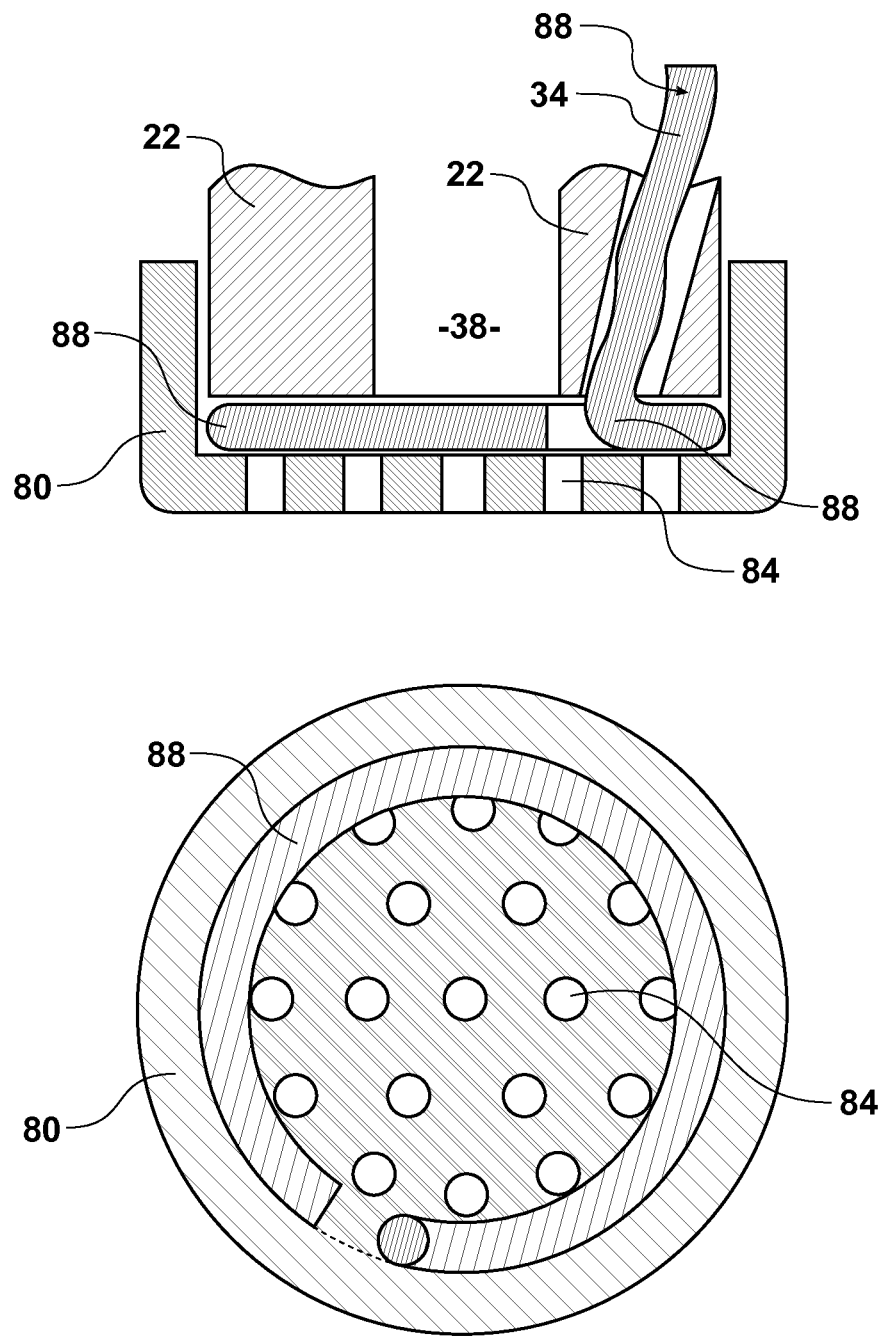
Figure 3- The Porous Cap

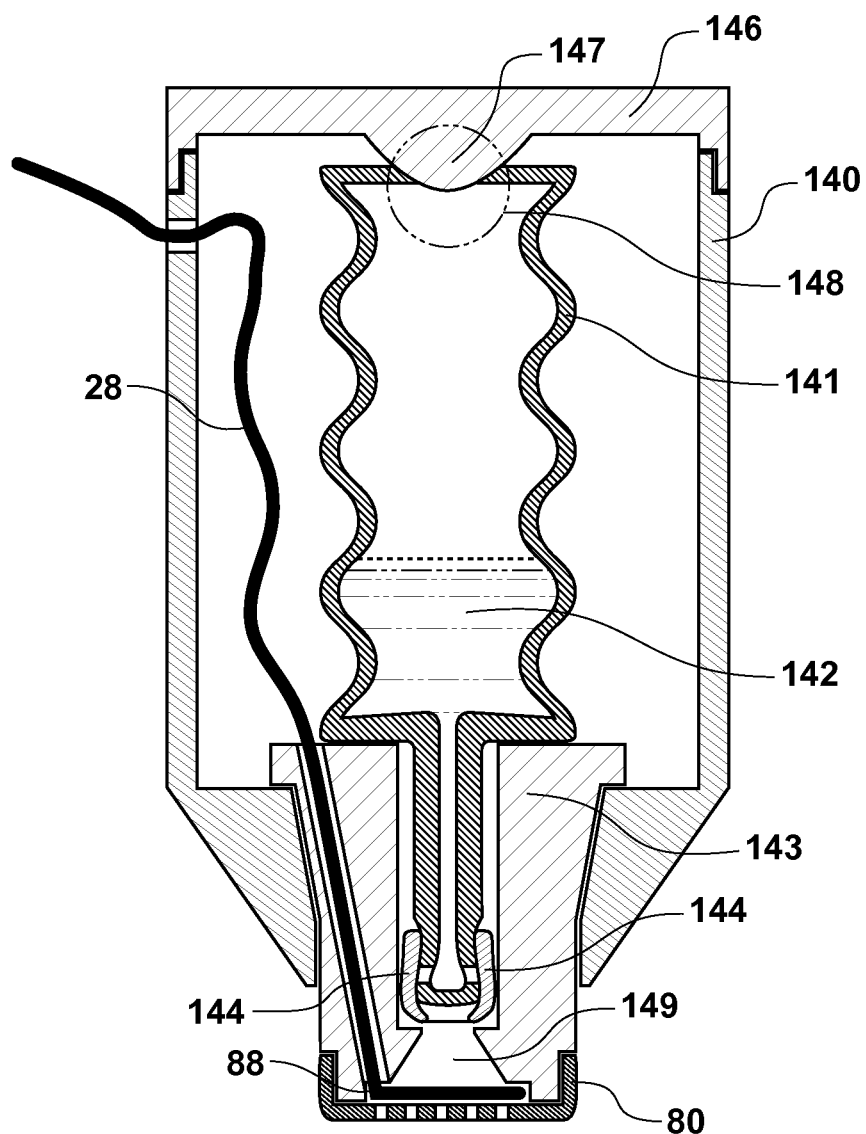
Figure 4- Corrugated Spring Cartridge Pencil

DYNAMIC PRECIOUS METAL ASSAY DEVICE

REFERENCES CITED

U.S. Patent Documents

U.S. Pat. No. 4,799,999 January 1989: DYNAMIC PRECIOUS METAL ASSAY METHOD
U.S. Pat. No. 5,218,303 January 1993: BROAD SPAN DYNAMIC PRECIOUS METAL ASSAY METHOD DRIVING ELECTRICAL PULSES THOUGHT AN ELECTROLYTE WET JUNCTION.
U.S. Pat. No. 6,051,126 April 2000: METHOD FOR ANALYZING PRECIOUS METALS
U.S. Pat. No. 5,128,016 July 1992: PRECIOUS METAL ANALYZER APPARATUS

OTHER PUBLICATIONS

Book

Dynamics Of Fluids In Porous Media by Jacob Bear, ©1972 Published by Dover 1988, ISBN 0-486-65675-6.

REFERENCE ARTICLES ON INTERNET

"ScrapGoldGuru.com, How to Make Money with Scrap Gold"
http://www.scrapgoldguru.com/electronic-gold-tester-review.
"Gold Testing Guide—electronic gold testers 101" by Igem: "Electronic Gold Tester Review"
http://reviews.ebay.com/Gold-Testing-Guide-electronic-old-testers-

BACKGROUND

The field of invention is primarily in CLASS 204, CHEMISTRY: ELECTRICAL AND WAVE ENERGY and subclass of PROCESSES AND PRODUCTS generally listed under analysis and testing likely within the 400s.

The parent patent, DYNAMIC PRECIOUS METAL ASSAY METHOD, U.S. Pat. No. 4,799,999 of Jan. 24, 1989 was a basic method which utilized the complex chemistry of time dependant electrochemistry to determine the alloy content of a gold specimen sample in units of karats. A galvanic cell integral to a device was produced by sending a pulse of current through an area wetted by an electrolyte between a reference electrode and the specimen sample electrode of a precious metal alloy. It was experimentally noted that this small galvanic cell had discharge properties that depended on the alloy of the test specimen sample electrode. This is an empirical phenomena that depends on the multidependant parameters of 1) current, 2) voltage, 3)time of current charge, 4) area of charged surfaces, 5) electrodes employed, 6) electrolyte employed, 7) volumetric parameters of the galvanic cell, and 8) and time dependant curve contour of the discharge rate of the galvanic cell. Because of the complexities of such a system, a heuristic analysis is used to determine the metric of the current meter on the device in units of the karat of a gold specimen sample. Over the ensuing 20 years since the parent patent was issued, the employees of Tri-Electronics Corporation has pursued a program of research and development on the parent method patent to manufacture an instrument to assure optimum performance in terms of ruggedness, economy of the expendable electrolyte and sensitivity and accuracy and competitive marketing. Currently, Tri-Electronics gold testing products are rated by experts as having the highest utility rating for professional use.("Gold Testing Guide—electronic gold testers 101" by Igem: and also "Electronic Gold Tester Review": on Internet). All gold testing patents issued in the class of said U.S. Pat. No. 4,799,999 make reference to this parent specification as the basic patent and the objectives of those succeeding patents are generally directed at attempts to optimize its performance in specific characteristics. However, because of the complex interactions of all parameters mentioned above, a modification in any singular aspect does affect other performance characteristics. This disclosure is the culmination of the extensive R&D of Tri-electronics to produce a superior device to any on the current market.

Specifically, U.S. Pat. Nos. 6,051,126 and 5,888,362 by Fegan, Jr. discloses using a permeable fiber interfacing wick for transporting an electrolyte between the reference electrode and the gold specimen sample. Fiber materials and the residual electrolyte held in the fiber were found to deteriorate prematurely and obfuscate the karat metric readout. The deteriorated fiber causes leakage from the devices causing valuable electrolytic loss as well as messy contamination.

U.S. Pat. No. 5,218,303 by Medvinsky, an employee of Tri-Electronics, further noted that the use of multiple successive pulses resulted in galvanic cell output metrics that increased the sensitivity of the basic device to the karat of gold alloy. However, it was only one of many potential algorithms possible and did not achieve the necessary specifications for a professional accurate tester.

In all circumstances, any change in the basic device requires extensive experimentation in respect to parametric changes in the other variables as mentioned above. In this sense, each such device is unique, though it complies with the methodology of the basic parent patent, DYNAMIC PRECIOUS METAL ASSAY METHOD, U.S. Pat. No. 4,799,999 of Jan. 24, 1989.

U.S. Pat. No. 5,128,016 of Moment merely utilizes steady state contact potential between dissimilar metals wetted with a defined electrolyte. This is classically known as the Galvani potential between two metals. Tri-Electronics initial research indicated such a system lacked the necessary sensitivity for the professional assay of gold alloys, though it is a classic method of confirming the identity of the elemental class of a conductor. This system has no value for professional use.

BRIEF SUMMARY OF THE INVENTION

The objective of the within preferred device embodiment for the methodology of the parent U.S. Pat. No. 4,799,999 takes into account minimizing the cost of manufacturing the device as well as increasing the accuracy and alloy sensitivity. The interpolating algorithm to determine the karat assay should also be kept as simple and direct as possible. The objective achieved in the within specification is a dependable device for accurately professionally assaying gold samples over 20 karat. The final prototypes are shown in the drawings and described in the following specification.

Tri-Electronics engaged in a R&D program after the granting of the parent patent DYNAMIC PRECIOUS METAL ASSAY METHOD, U.S. Pat. No. 4,799,999 of Jan. 24, 1989. The company examined the competitive products on the market and also had feedback from its customers. Based on all the information as well as the experimental program, it was realized that the corrosive electrolyte inevitably caused accelerated decay of any permeable wicking material intended to transport the electrolyte to the tip. In addition, the placement of the active part of the reference electrode at a relatively large distance (and without reproducible placement) from the test specimen electrode resulted in a polarization of the reference electrode as well as ionic depletion of the residual electrolyte between the reference electrode and the specimen sample electrode and within any permeable wick media. The uncertain geometry of the galvanic cell does invalidate the algorithm of the electronic readout resulting in inaccurate readings. A further problem was the potential contamination of the electrolytic substance in a bulk container. The electrolyte dispensing system on the existing gold testing devices was also a bit sloppy and not well controlled, resulting in costly waste of the electrolyte and often staining of the test specimen. Often, this sloppiness resulted in a varying pattern of contact with the specimen sample and staining of a valuable piece of jewelry. Cleaning of the marketed gold testers was also difficult and really a factory maintenance operation. A more critical problem was that the accuracy of the instruments was poor at high gold karat values, and that assay range is of greatest interest for professional users. Extensive experimentation clearly indicated that the sensitivity of the metric increased as the dimensions of the galvanic cell became smaller. This necessitated a program of testing various electrode geometries so as to assure close tolerances and repeatability of each test procedure. The herein proposed improvement device embodiment on the method of the parent U.S. Pat. No. 4,799,999 is the end result of this extended R&D program and speaks to the current optimization of the marketable product.

The improvements included the following considerations.

A precision and controlled feed of the electrolyte solution was needed to avoid costly waste and staining. This is now accomplished by two systems:
  a) a unidirectional rotatable knob that mates with a threaded shaft which drives a piston in a cartridge containing electrolyte;
  b) a sliding block attached to the lower part of the test pencil that is pressed against a test specimen to pinch an accordion springing cartridge of electrolyte and release electrolyte.

The screw pitch meters out the exact amount of electrolyte to the galvanic cell and the travel of the sliding block squeezes out an exact amount of electrolyte to the galvanic cell.

The electrolyte is contained in a sealed disposable cartridge, so no electrolyte is ever handled in bulk. This avoids contamination and costly spills of a toxic material as well as waste disposal control.

The body of the gold tester is a rugged casing which holds the disposable cartridge in a locked position and also has a removable porous cap tip. The casing encloses a wire feed channel for the reference electrode wire that goes to the tip where the reference electrode wire is circumferentially wrapped into the reference electrode in the removable porous cap which comprises the galvanic cell.

A removable porous cap is attached to the bottom of the casing. This porous cap is capable of holding electrolyte by surface tension and capillary action in and on its porous surface. The perforated mesh or pattern on the bottom of the cap is to be positioned against the test specimen. This system assures uniformity of specimen contact of a repeatable wetted contact with the specimen electrode as well as tight control of the geometry of the galvanic cell.

External to the precious metal device pencil assembly is the electronics program box which contains programmed circuitry to initiate electric pulses which are fed to the reference electrode wire and test specimen sample. There are three programs:
  a) the charging program is to activate the galvanic cell;
  b) the readout program to monitor voltage and current of the galvanic cell during charging and discharging, and annunciate its analysis in terms of karat content of the test specimen;
  c) the depolarizing program of a reversed voltage pulse (in respect to charging program) to remove any residual electrolytic or reference electrode contamination that may occur in the galvanic cell.

The creation of a miniature galvanic cell structure within the attached porous cap when the test specimen is placed in contact with the bottom of the perforated mesh of the cap and there is electrolyte filling the cap and saturating the porous perforated mesh so as to also contact the test specimen. The active galvanic cell is formed by the charging cycle from the electronics program box and that cell is between the ring of wire attached to the reference electrode wire and the test specimen sample.

The utilization of the piston drive or compressible cartridge assures conservative use of the electrolyte and precision control of the amount of electrolyte released to the galvanic cell. The improvement of the disposable cartridge assures avoidance of external contamination that can occur to bulk electrolytes.

The utilization of a casing assures easy maintenance and ruggedness. In addition, the drilling of a wire feed channel for a free reference electrode wire that attaches to the ring of wire assures easy replacement of this precious metal reference electrode.

The utilization of a removable porous cap of inert material which fits tightly on the bottom of the casing against the ring of wire reference electrode assure the existence of a miniature galvanic cell of close precision dimensions which may be maintained by occasionally removing and washing or replacement. This miniature galvanic cell can also be totally and sparingly flushed of all electrolyte subjected to the testing cycle. The nature of the wetting characteristics associated with the capillary action of the mesh assures a limited and precision wetting of the test area on the test specimen.

The utilization of a miniature galvanic cell results from the novel porous cap in this type of instrument. The technical subject of porosity is well covered in the seminal engineering text of *Dynamics Of Fluids In Porous Media* by Jacob Bear, ©1972 Published by Dover 1988, ISBN 0-486-65675-6. The importance of porosity is that a porous material holds liquids and is technically distinguishable from a permeable material which transports liquids. Porosity is a characteristic feature of sponges, chamois and blotters; permeability is a characteristic of felt, cotton and other fiber materials intended as wicks. Because of the physics of capillary action and surface tension it is very difficult to wash clean a permeable material and much easier to flush a porous material. In the within embodiment, the feature of flushing the used electrolyte is critical in maintaining the accuracy of this precious metal tester. Hence, the importance of porosity for holding a repeatable small quantity of electrolyte for contact with the external test specimen. The ability to easily replace the porous cap is also critical. Though porous media is generally available, it is best to manufacture a porous cap by a precision pattern of perforations in a material known to be inert to the electrolyte.

The utilization of a depolarizing program restores the electrically active regions to its initial state so as to reset the metric of the readout program.

BRIEF DESCRIPTION OF THE DRAWINGS

FIG. 1, The Pencil Assembly and External Electronics Box depicts the central vertical cross sectioned view of the threaded piston version of the precious metal assay testing pencil showing the components of the turning knob top, casing, cartridge, porous cap, precious metal test specimen and external electronic program (black) box.

FIG. 2 The Expendable Piston Cartridge is a vertical view of the details of the electrolytic cartridge that is inserted into the casing.

FIG. 3 The Porous Cap shows horizontal internal view of a perforated removable cap that attaches to the bottom of the casing and encloses the ring of wire reference electrode of the miniature galvanic cell.

FIG. 4 Corrugated Spring Cartridge Pencil shows the assembly of a springing corrugated cartridge, casing, top cap, and Porous Cap. In this modified version, the pressing of test pencil against the test specimen compresses the corrugated cartridge causing an expulsion of electrolyte into the galvanic cell located in the Porous Cap.

DETAILED DESCRIPTION AND MODE OF OPERATION

FIG. 1; The Pencil Assembly and External Electronics Box

The assembled DYNAMIC PRECIOUS METAL ASSAY DEVICE is depicted in FIG. 1. The major assemblies are comprised of the electrolyte Cartridge Assembly 50 which fits securely in the Casing Assembly 20 which has a Top Cap Assembly 2 for feed control and a Porous Cap Assembly 80 for retaining electrolyte against a Test Specimen Electrode 90. The functioning device is powered by the Control And Readout Interface 100 which contains electronic circuitry that produces the polarizing pulses and interpolation of the output signal in terms of karats of precious metal.

The assembled unit of said Top Cap Assembly 2, Casing Assembly 20, Cartridge Assembly 50, and Porous Cap Assembly 80 comprise the testing pencil. The testing pencil and Test Specimen Electrode 90 are electrically connected to the Control And Readout Interface 100 which contains the electronic algorithm and readout display in units of gold karats. The procedure for assaying a precious metal specimen requires that some piece of jewelry which becomes the Test Specimen Electrode 90 (which is connected to the Control And Readout Interface 100) is held against the bottom of the Porous Cap Assembly 80 and the Feed Knob 4 be turned to extrude a bit of electrolyte onto the said Test Specimen Electrode 90. A control button on the Control And Readout Interface 100 is pushed and shortly thereafter the readout displays the assay in units of karats. This is a fast, accurate and economical non-destructive method of assaying a precious metal sample or piece of jewelry. It is a rugged and basically simple commercial unit intended for professional use, though the technical theory behind its function is rather sophisticated. The functionality of this device has been well established by the parent patent DYNAMIC PRECIOUS METAL ASSAY METHOD, U.S. Pat. No. 4,799,999 but the within embodiment has specific novel improvements which make this unit superior to all other commercial units, and these improvements are described and shown in detail below.

The Casing Assembly 20

The Casing Assembly 20 which is depicted in FIG. 1 is a rugged cast plastic cylindrical tube into which a disposable syringe cartridge may be inserted. Here the Cartridge Assembly 50 is sealed into the Casing 22 by a Top Cap Assembly 2. A reference electrode wire that that directs current from the Control And Readout Interface 100 to the electrolyte within the Porous Cap Assembly 80 is an assembly comprised of a Casing Wire 28 enclosed in a Wire Conduit 30 and joined to the Reference Electrode 88 by a Weld Joint 32. The wire material that is employed for the said Reference Electrode 88 is a precious metal (platinum). The use of a Weld Joint 32 to an inexpensive lead wire such as intended as the Casing Wire 28 saves replacement costs. This precious metal wire lead terminates as the Reference Electrode 88 in the configuration of a circle which fits circumferentially within the Porous Cap Assembly 80 as illustrated in FIG. 3; THE POROUS CAP.

The Top Cap Assembly 2

The Top Cap Assembly 2 which attaches to the top section of the Casing Assembly 20 at the Top Casing Junction 16 contains a simple unidirectional rotational system of Cog Gear 6 and Unidirectional Cog 8 which engage by pressure from the Engagement Spring 10 in response to a measured rotation of the Feed Knob 4. The horizontal cross-section shown in insert B shows the mating link (which is the Flat Pivot 54 as shown in FIG. 2; THE EXPENDABLE PISTON CARTRIDGE) in the Pivot Disk 12 that will engage the Cartridge Assembly 50. As to be described in detail in the following section describing FIG. 2, the measured turn of the Feed Knob 4 which is transmitted the Pivot Disk 12 will result in the expulsion of fresh electrolyte from the Cartridge Assembly 50 through the Electrolyte Feed Tube 68 channeled down into the small void of the attached Porous Cap Assembly 80. The key essential item for the sensitive and accurate assay of a precious metal sample is the existence of the small dimensioned galvanic cell which is formed in this small void at the tip of the test pencil.

FIG. 2; The Expendable Piston Cartridge

The Cartridge Assembly 50 is depicted in both FIGS. 1 and 2. Reference is now made to FIG. 2 which shows a vertical central cross section of cartridge ready for insertion into a casing. Horizontal sectional views 2A and 2B show the Shaft Pinion 66 encompassing the Threaded Shaft Retainer 64 and the Horizontal Retaining Ribs 70 exterior to the Cartridge Wall 52. The insert A depicts the system that assures alignment of a Threaded Shaft 56 and insert B depicts the system that assures the Cartridge Assembly 50 does not rotate when the Threaded Shaft 56 is rotated.

A Flat Pivot 54 which penetrates through the top of the Cartridge Wall 52 is to engage the Pivot Disk 12 of FIG. 1 in the Top Cap Assembly 2. This Flat Pivot 54 rotates a Threaded Shaft 56. On the Threaded Shaft 56 floats a Piston Nut 58 which pushes a Piston Seal 60 expelling Electrolyte 62 from the Cartridge Assembly 50 through the Electrolyte Feed Tube 68. The pitch on the Threaded Shaft 56 assures precision control of expelling electrolyte.

The employment of a sealed cartridge is a major improvement over the parent U.S. Pat. No. 4,799,999 which used bulk electrolyte. All electrolytes used are corrosive and toxic and must be contained and controlled. They are also subject to contamination, so must be hermetically sealed until used. Contamination does influence the electronic performance of the electrolyte and results in an erratic register from the readout program. In addition, the electrolyte must be dispensed in precision amounts into the galvanic cell. This Cartridge Assembly 50 in its pencil is an improvement that achieves all these goals. Other sealed cartridge assemblies are also under investigation. Another type of pencil that employs an accordion wall which may be compressed inside an appropriate casing to expel electrolyte will be discussed below in FIG. 4. The point of invention is that a controlled expulsion of a small amount of electrolyte from a sealed disposable cartridge into a miniature galvanic cell for wetting a test specimen through a porous membrane as proposed in the parent patent, DYNAMIC PRECIOUS METAL ASSAY METHOD, U.S. Pat. No. 4,799,999 of Jan. 24, 1989, and described in this device specification in a DYNAMIC PRECIOUS METAL ASSAY DEVICE assures an accurate professional quality reading of karat content heretofore not achieved by any device based on that parent patent DYNAMIC PRECIOUS METAL ASSAY METHOD, U.S. Pat. No. 4,799,999 of Jan. 24, 1989.

FIG. 3; The Porous Cap

The use of a Porous Cap Assembly 80 instead of a permeable wick, such as a felt fiber is an important innovation in this precious metal device technology. The long standing problems associated with both contacting the electrolyte to the specimen sample as well as transporting fresh supplies of electrolyte to the galvanic cell is alleviated by capturing the electrolyte onto a porous surface in a small galvanic cell. The complex technology of matching the surface tension of the liquid to the capillary action associated with the cavities of a porous material is best solved by laboratory experimentation. This had been done during extensive R&D by Tri Electronics Corporation. This simple solution is the assembly depicted in FIG. 3.

FIG. 3 shows the Porous Cap Assembly 80 in vertical and horizontal sections. This Porous Cap Assembly 80 fits snugly over the Tip Channel 38 on the Casing 22 creating a void which contains ejected electrolyte. The void has dimensions created by the diameter of the Reference Electrode 88 which is actually just a circular wrap of the said precious metal platinum wire that fits circumferentially into the Porous Cap Assembly 80. This small and tight void in conjunction with contained Electrolyte 62 and the two electrodes of the Reference Electrode 88 and a Test Specimen Electrode 90 shown on FIG. 1 form the very well defined and highly sensitive galvanic cell which has been shown to accurately measure the precious metal content in gold karats. It is also cleanable and economical in the consumption of electrolyte and assures a small reproducible electrical contact with any valuable piece of jewelry under test.

As mentioned above, the material and perforations of the Porous Substrate 84 has been researched by the inventors and has resulted in a selection of many materials and patterns all of which are inter-related to the surface tension of the electrolyte.

FIG. 4 Corrugated Spring Cartridge Pencil

Another way of achieving the objectives of this DYNAMIC PRECIOUS METAL ASSAY DEVICE suggested the employment of a dispensable Spring Corrugated Cartridge 141, which restores itself to its initial configuration when not under compression. FIG. 4 employs the critical Porous Cap Assembly 80 as shown in FIG. 3 with associated electronic connections of Casing Wire 28 to Reference Electrode 88 as shown in FIG. 1. As mentioned above in the FIG. 2; THE EXPENDABLE PISTON CARTRIDGE, this FIG. 4 introduces another version of a cartridge and compatible casing.

A compression of said Spring Corrugated Cartridge 141 occurs when compressed between the Sliding Bottom Block 143 and the Top Seal 146. The Sliding Bottom Block 143 also serves as mounting base for the sensor assembly of Porous Cap Assembly 80 as well as a conduit for Electrolyte Feed Tube 68 as described in the prior sections. The significant difference in this casing assembly is that said Sliding Bottom Block 143 is an actuator that pushes the bottom of the Spring Corrugated Cartridge 141 when pressed against a test specimen such as a piece of gold jewelry. The travel distance of the Sliding Bottom Block 143 when it becomes level with the bottom of the Corrugated Casing 140 causes an expulsion of a measured amount of electrolyte into the Electrolyte Feed Tube 68 which has an Elastic Valve 144 at its tip which assures a unidirectional metered amount of electrolyte goes into Sensor Chamber 149. The Spring Corrugated Cartridge 141 is easily removable when the Top Seal 146 of Corrugated Casing 140 is opened. The Top Seal 146 has a Spherical Bulge 147 on the inside which seals a Round Opening 148 at the top of the Spring Corrugated Cartridge 141. This combination of congruent Spherical Bulge 147 and Round Opening 148 works as a valve which lets air into the cartridge to replace the extruded electrolyte.

This specified configuration also achieves the objectives of this DYNAMIC PRECIOUS METAL ASSAY DEVICE by assuring a metered fresh small amount of electrolyte is extruded from a replaceable sealed cartridge into a small galvanic cell.

We claim:

1. A dynamic precious metal assay device which comprises the components of:
    a casing assembly with electrical junctions;
    a disposable replaceable cartridge assembly which is inserted into said casing assembly and
        containing electrolyte solution and having a electrolyte exit channel and means of manually expelling measured amounts of said electrolyte;
    a top cap which seals said disposable replaceable cartridge assembly into said casing assembly;
    a porous cap assembly which contains a reference electrode that is joined to said electrical junctions of said casing assembly and porous perforations on the lower extremity of said porous cap with said porous cap assembly being attached to the lower extremity of said casing and contiguous to the electrolyte exit channel of said inserted disposable replaceable cartridge assembly so as to receive the metered manually ejected electrolyte;
    an electrically conducting test specimen held against porous perforations on the bottom extremity of said porous cap and wetted by said electrolyte and thereby forming a small galvanic cell with said porous cap assembly; and
    external electronics containing control and readout circuitry capable of pulsing an electric current from said reference electrode through said electrolyte to said wetted test specimen and said readout circuitry having means to interpolate the ensuing electric discharge of said galvanic cell in terms of gold karats;
    whereby the device is capable of electronically analyzing a gold test specimen in terms of karat alloy located at the manually ejecting electrolyte and wetting contact point between said test specimen and said porous cap which retains electrolyte by surface tension within the well defined geometry of said galvanic cell.

2. A dynamic precious metal assay device as described in claim 1 in which
    said top cap assembly has a unidirectional rotatable knob containing cogs and cams and a means of making a junction to a threaded shaft screw drive;
    a disposable replaceable cartridge assembly containing electrolyte which has
        a threaded shaft screw drive which mates with said top cap assembly;
        a compatible threaded piston nut which tides on said threaded shaft screw drive;
        a piston seal which is seated on said threaded piston nut and wipes the wall of said disposable replaceable cartridge; and a fluid channel for electrolyte that expels said electrolyte into said porous cap assembly;

whereby a turning of said unidirectional rotatable knob manually ejects a metered amount of electrolyte into said porous cap assembly assuring said test specimen is wetted by fresh manually ejected electrolyte.

3. A dynamic precious metal assay device as described in claim 1 in which said disposable replaceable cartridge assembly is a flexible corrugated tubular container of electrolyte with an air inlet valve means and a fluid ejection valve means on said electrolyte exit channel;

and said casing assembly having a sliding block that is captive on its lower extremity which slips into the shell of said casing and has a contiguous chamber to said electrolyte exit channel that conducts electrolyte into said porous cap assembly;

whereby contacting the sliding block at the lower extremity of said casing and pressing against said test specimen causes the sliding block to compress the said flexible corrugated tubular container of the said disposable replaceable cartridge against the said top cap resulting in a manual ejection of electrolyte into said porous cap assembly and wetting said test specimen.

* * * * *